(12) United States Patent
Bhattacharyya et al.

(10) Patent No.: US 9,085,522 B2
(45) Date of Patent: Jul. 21, 2015

(54) PROCESS FOR PRODUCING TEREPHTHALIC ACID

(75) Inventors: Alakananda Bhattacharyya, Glen Ellyn, IL (US); Raymond C. Shih, Elgin, IL (US)

(73) Assignee: UOP LLC, Des Plaines, IL (US)

( * ) Notice: Subject to any disclaimer, the term of this patent is extended or adjusted under 35 U.S.C. 154(b) by 307 days.

(21) Appl. No.: 13/340,132

(22) Filed: Dec. 29, 2011

(65) Prior Publication Data
US 2013/0172606 A1    Jul. 4, 2013

(51) Int. Cl.
| C07C 51/265 | (2006.01) |
| B01J 19/00 | (2006.01) |
| B01J 19/18 | (2006.01) |
| B01J 4/00 | (2006.01) |

(52) U.S. Cl.
CPC ............... *C07C 51/265* (2013.01); *B01J 4/002* (2013.01); *B01J 19/006* (2013.01); *B01J 19/1812* (2013.01); *B01J 19/1862* (2013.01); *B01J 19/1875* (2013.01); *B01J 2219/0004* (2013.01); *B01J 2219/00006* (2013.01); *B01J 2219/00166* (2013.01)

(58) Field of Classification Search
USPC .................................. 562/412, 416
See application file for complete search history.

(56) References Cited

U.S. PATENT DOCUMENTS

| 4,334,086 | A | 6/1982 | Hanotier et al. |
| 5,359,133 | A | 10/1994 | Nazimok et al. |
| 5,840,968 | A | 11/1998 | Lee et al. |
| 7,390,928 | B2 | 6/2008 | Hobbs et al. |
| 7,485,747 | B2 * | 2/2009 | Sheppard et al. ............. 562/487 |
| 7,985,875 | B2 | 7/2011 | Hashmi et al. |
| 2001/0041811 | A1 | 11/2001 | Sikkenga |
| 2003/0229247 | A1 | 12/2003 | Housley |
| 2004/0015009 | A1 | 1/2004 | Earle |
| 2005/0107630 | A1 | 5/2005 | Belmonte |
| 2006/0173221 | A1 | 8/2006 | Hagiya |
| 2007/0010688 | A1 | 1/2007 | Ko |
| 2007/0155985 | A1 | 7/2007 | Wonders et al. |
| 2007/0208193 | A1 * | 9/2007 | Wonders et al. ............. 562/410 |
| 2008/0191170 | A1 | 8/2008 | Walker et al. |
| 2009/0326265 | A1 * | 12/2009 | Hashmi et al. ............. 562/416 |
| 2010/0174111 | A1 | 7/2010 | Rogers et al. |
| 2010/0200804 | A1 | 8/2010 | Woodruff et al. |
| 2013/0172607 | A1 | 7/2013 | Bhattacharyya |
| 2013/0172611 | A1 | 7/2013 | Bhattacharyya |
| 2013/0172613 | A1 | 7/2013 | Bhattacharyya |

FOREIGN PATENT DOCUMENTS

| CN | 1512976 A | 7/2004 |
| CN | 101613319 A | 12/2009 |
| KR | 20100039554 A | 4/2010 |
| TW | 200927720 A | 7/2009 |

OTHER PUBLICATIONS

Search Report dated Jan. 16, 2014 for ROC (Taiwan) Patent Application No. 101141406.
Search Report dated Feb. 12, 2014 for ROC (Taiwan) Patent Application No. 101141405.
International Search Report for PCT/US2012/060704, mailing date Feb. 21, 2013.
International Search Report for PCT/US2012/060715, mailing date Mar. 6, 2013.
International Search Report for PCT/US2012/060724, mailing date Feb. 28, 2013.
International Search Report for PCT/US2012/060733, mailing date Jan. 17, 2013.

* cited by examiner

*Primary Examiner* — Kamal Saeed
*Assistant Examiner* — Janet L Coppins

(57) ABSTRACT

Methods and apparatus for producing terephthalic acid using a p-xylene stream enriched with p-toluic acid are described. The apparatus includes first and second reactor zones. The reactor zones can be in the same reactor or in different reactors.

10 Claims, 6 Drawing Sheets

US 9,085,522 B2

PROCESS FOR PRODUCING TEREPHTHALIC ACID

FIELD OF THE INVENTION

This invention relates to terephthalic acid compositions and processes for producing terephthalic acid from a feedstock comprising para-xylene. More particularly, the invention relates to processes and apparatus for the oxidation of a p-xylene stream enriched with p-toluic acid to produce terephthalic acid.

BACKGROUND OF THE INVENTION

Oxidation of alkyl aromatic compounds, e.g., toluene and xylenes, are important commercial processes. A variety of oxidation products may be obtained including aromatic carboxylic acids such as terephthalic acid (1,4-benzenedicarboxylic acid) and isophthalic acid (1,3-benzenedicarboxylic acid) which are used, for example, in the polymer industry.

It is known that oxidation products, such as aromatic alcohols, aromatic aldehydes, aromatic ketones, and aromatic carboxylic acids, may solidify or crystallize at oxidation conditions and/or as the reaction mixture cools. Thus, mixtures of oxidation products may be produced which require further processing to increase the purity of the desired product. For example, in the production of terephthalic acid, the oxidation product is often referred to as crude terephthalic acid because it contains impurities including color bodies and intermediate oxidation products, especially 4-carboxybenzaldehyde (4-CBA). To obtain polymer grade or purified terephthalic acid, various purification steps are known in the art including: washing the crude terephthalic acid with water and/or a solvent, additional oxidation or crystallization steps, and reacting a solution of dissolved crude terephthalic acid with hydrogen at hydrogenation conditions usually including a catalyst comprising palladium and carbon. Often several purification steps are used.

U.S. Pat. No. 2,833,816 discloses processes for oxidizing aromatic compounds to the corresponding aromatic carboxylic acids. A process for the liquid phase oxidation of alkyl aromatic compounds uses molecular oxygen, a metal or metal ions, and bromine or bromide ions in the presence of an acid. The metals may include cobalt and/or manganese. Exemplary acids are lower aliphatic mono carboxylic acids containing 1 to 8 carbon atoms, especially acetic acid.

U.S. Pat. No. 6,355,835 discloses a process for the preparation of benzene dicarboxylic acids by liquid phase oxidation of xylene isomers using oxygen or air by oxidizing in the presence of acetic acid as a solvent, a cobalt salt as a catalyst, and an initiator. The oxidation step is followed by flashing the reaction mixture to remove volatile substances and cooling and filtering the material to get crude benzene di-carboxylic acid as a solid product and a filtrate. Recrystallizing the crude benzene di-carboxylic acid to obtain at least 99% purity and recycling of the filtrate are also disclosed.

U.S. Pat. No. 7,094,925 discloses a process for preparing an alkyl-aromatic compound. The process includes mixing an oxidizing agent or sulfur compound in the presence of an ionic liquid. Air, dioxygen, peroxide, superoxide, or any other form of active oxygen, nitrite, nitrate, and nitric acid or other oxides or oxyhalides of nitrogen (hydrate or anhydrous) can be used as the oxidizing agent. The process is typically carried out under Bronstead acidic conditions. The oxidation is preferably performed in an ionic liquid containing an acid promoter, such as methanesulfonic acid. The product is preferably a carboxylic acid or ketone or intermediate compound in the oxidation, such as an aldehyde, or alcohol.

U.S. Pat. No. 7,985,875 describes a process for preparing an aromatic polycarboxylic acid by liquid phase oxidation of a di- or tri-substituted benzene or naphthalene compound. The process involves contacting the aromatic compound with an oxidant in the presence of a carboxylic acid solvent, a metal catalyst, and a promoter in a reaction zone. The promoter is an ionic liquid comprising an organic cation and a bromide or iodide anion. The promoter is used in a concentration range of about 10 to about 50,000 ppm (based on solvent) with a preferred range of 10-1,000 ppm. No other promoters, such as bromine-containing compounds, need to be used in the process. The process produces crude terephthalic acid (CTA) having 1.4-2.2% 4-CBA. Purification of the CTA is required to obtain purified terephthalic acid (PTA).

US 2010/0174111 describes a process for purifying aryl carboxylic acids, such as terephthalic acid. The impure acid is dissolved or dispersed in an ionic liquid. A non-solvent (defined as a molecular solvent for which the ionic solvent has high solubility and for which the aryl carboxylic acid has little or no solubility) is added to the solution to precipitate the purified acid.

U.S. Pat. No. 7,692,036, 2007/0155985, 2007/0208193, and 2010/0200804 disclose a process and apparatus for carrying out the liquid-phase oxidation of an oxidizable compound. The liquid phase oxidation is carried out in a bubble column reactor that provides for a highly efficient reaction at relatively low temperatures. When the oxidized compound is para-xylene, the product from the oxidation reaction is CTA which must be purified. Purification is said to be easier than for conventional high temperature processes.

SUMMARY OF THE INVENTION

The invention provides a process for the oxidation of paraxylene to terephthalic acid. It has been discovered that the invention may be used to produce terephthalic acid compositions having different amounts of contaminants relative to those observed in conventional processes. In some embodiments, the terephthalic acid compositions produced by the process have low levels of impurities and thus are less costly to purify. In some embodiments, the invention produces polymer grade or purified terephthalic acid without the use of catalytic hydrogenation.

One aspect of the invention is a process for producing terephthalic acid. In one embodiment, the process includes contacting p-xylene, a first solvent comprising a carboxylic acid, a first bromine source, a first catalyst, and a first oxidizing agent in a first reaction zone to produce a p-xylene stream enriched with p-toluic acid; and contacting the p-xylene stream enriched with p-toluic acid, a second solvent comprising an ionic liquid, a second bromine source, a second catalyst, and a second oxidizing agent in a second reaction zone to produce a product comprising terephthalic acid.

Another aspect of the invention involves an apparatus for oxidizing alkyl-aromatic compounds. In one embodiment, the apparatus includes a first reaction zone having at least one inlet and at least one outlet; a second reaction zone having at least one inlet and at least one outlet, at least one second reaction zone inlet in fluid communication with at least one first reaction zone outlet; and a purification zone having at least one inlet and at least one outlet, at least one purification zone inlet in fluid communication with at least one second reaction zone outlet, and at least one purification zone outlet in fluid communication with at least one first reaction zone inlet, or at least one second reaction zone inlet, or both.

DETAILED DESCRIPTION OF THE INVENTION

In general, the invention relates to terephthalic acid compositions and processes for the oxidation of para-xylene to terephthalic acid. In broad terms, the invention is a process for producing terephthalic acid from a p-xylene stream enriched with p-toluic acid.

As discussed below, it was discovered that the production of 4-CBA is significantly lower if the starting material is p-toluic acid rather than p-xylene. As a result, it was determined that starting with a p-xylene feed stream enriched with p-toluic acid would be desirable.

Figure 1:
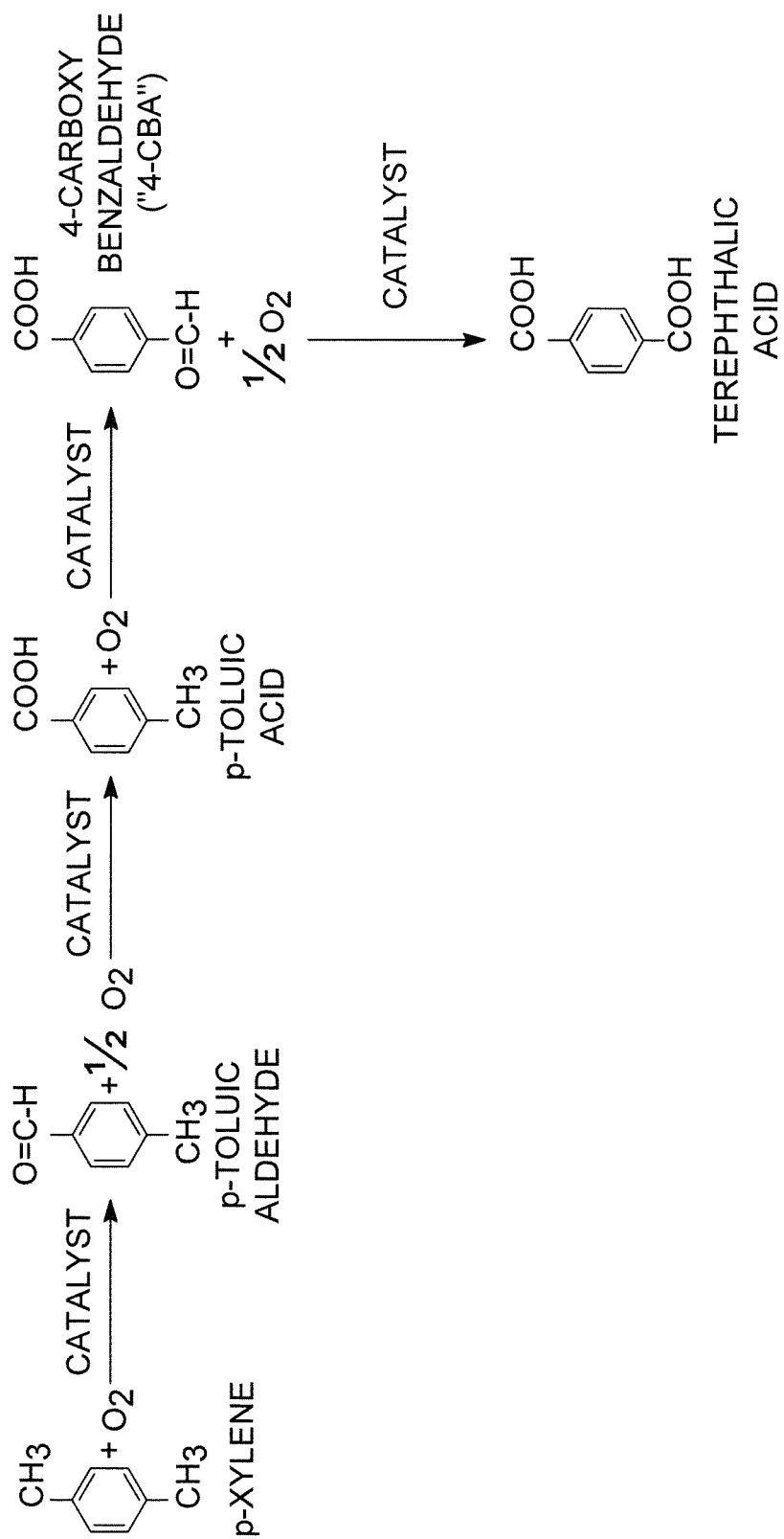
FIG. 1 is a reaction scheme for the oxidation of p-xylene.

In addition, the general reaction scheme for the production of terephthalic acid through liquid-phase oxidation of p-xylene is shown in FIG. 1. In that series of reactions, the production of p-toluic acid from p-xylene is faster in acetic acid than it is in ionic liquid. However, the subsequent reactions are faster and more selective in an ionic liquid/acetic acid mixture than in acetic acid alone.

The p-xylene stream enriched with p-toluic acid can be obtained in any suitable manner, including but not limited to, oxidation, alkylation and the like. For example, a stream having the required p-toluic acid content could be generated as a product stream in a petroleum or chemical processing complex, as described below. If the initial product stream does not have the needed purity, it can be purified to the desired level using known methods.

The p-xylene stream enriched with p-toluic acid contains at least about 5% and less than 90% by weight p-toluic acid. It typically contains at least about 10% by weight, or at least about 15% by wt, or at least about 20% by weight, or at least about 25% by wt, or at least about 30% by weight, or at least about 35% by wt, or at least about 40% by weight, or at least about 45% by wt, or at least about 50% by weight, or at least about 55% by wt, or at least about 60% by wt, or at least about 65% by weight, or at least about 70% by wt, or at least about 75% by wt. It can contain less than about 85% wt, or less than about 80% wt, or less than about 75% wt, or less than about 70% wt, or less than about 65% wt, or less than about 60% wt, or less than about 55% wt, or less than about 50% wt, or less than about 45% wt, or less than about 40% wt.

The p-toluic acid level is maintained in solution, as colloids, or as a slurry.

The basic step of the process involves contacting the p-xylene stream enriched with p-toluic acid (however obtained), a solvent comprising an ionic liquid, a bromine source, a catalyst, and an oxidizing agent to produce a product comprising terephthalic acid.

The contacting step(s) may be practiced in laboratory scale experiments through full scale commercial operations. The process may be operated in batch, continuous, or semi-continuous mode. The contacting step can take place in various ways. The order of addition of the components (e.g. p-xylene stream enriched with p-toluic acid, solvent, bromine source, catalyst, and oxidizing agent) is not critical. For example, the components can be added individually, or two or more components may be combined or mixed before being combined or mixed with other components.

Figure 2:
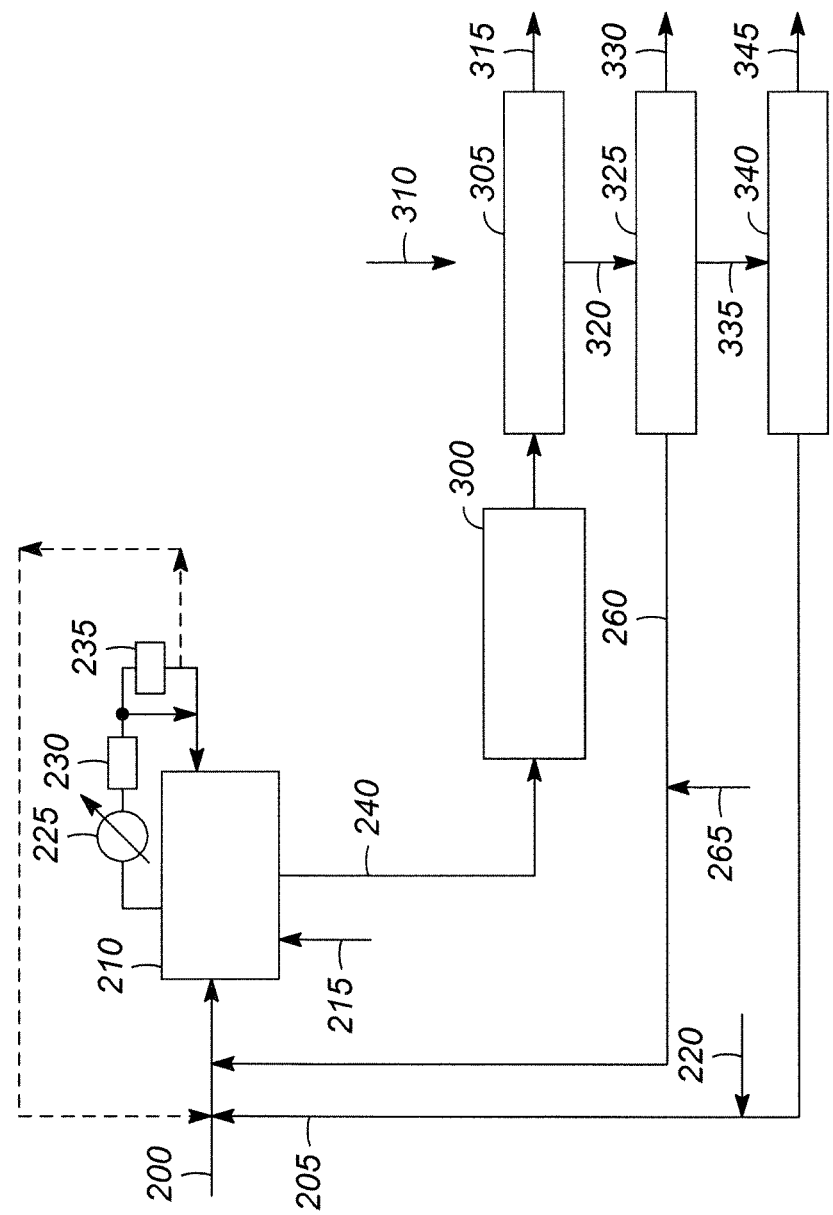
FIG. 2 is a general process flow diagram for one embodiment of a process for producing purified oxidized alkyl aromatic compounds.

FIG. 2 is a general process flow diagram for an embodiment of a process for producing purified oxidized alkyl aromatic compounds.

The feed 200 is introduced into oxidation zone 210 along with an oxidizing agent 215. An overhead condenser 225 removes heat from the reflux stream to control reaction zone temperature, and an absorption zone 230 and dehydration zone 235 remove offgas and water from the reaction zone.

Effluent liquid 240 from the oxidation zone 210 is sent to a crystallization zone 300 to complete the crystallization process. The crystallization zone 300 can include one or more post reaction zones and/or one or more crystallizers. If a post reaction zone is needed to increase conversion further, additional oxidizing agent will be required. The post reaction zone can operate at lower pressure and lower temperature to help with crystallization. One or more crystallizers are used to complete the crystallization of the product, such as terephthalic acid at lower temperatures. Care should be taken not to co-crystallize impurities. The solvent comprising ionic liquids provides a medium where the impurities and/or intermediates remain in the solvent or are further oxidized to terephthalic acid, thereby substantially reducing the co-crystallized impurities.

The crystallized product is separated from the solvent in a separator zone 305. The separator zone 305 can include one or more of filters, centrifuges, and dryers, as is known in the art.

Solvent 310 is used to wash the product crystals in the separator zone 305. The purified product 315 is dried and stored in a product silo. An additional separation device may be needed to ensure that the product meets the product specification before storage.

The washed mother liquor 320 is sent to solvent separator zone 325. The solvent separation can include one or more of evaporators, distillation and/or fractionation columns, membrane separators and the like, as are known to those of skill in the art, The ionic liquid 260 is recycled back to the oxidation zone 210. Make-up ionic liquid 265 can be added as needed.

The catalyst 330 is sent for catalyst recovery.

The carboxylic acid solvent 335 is dehydrated in a dehydration zone 340. The carboxylic acid solvent 205 can be recycled back to the oxidation zone 210. Make-up carboxylic acid solvent 220 can be added if needed. The waste water 345 is removed.

Figure 3:
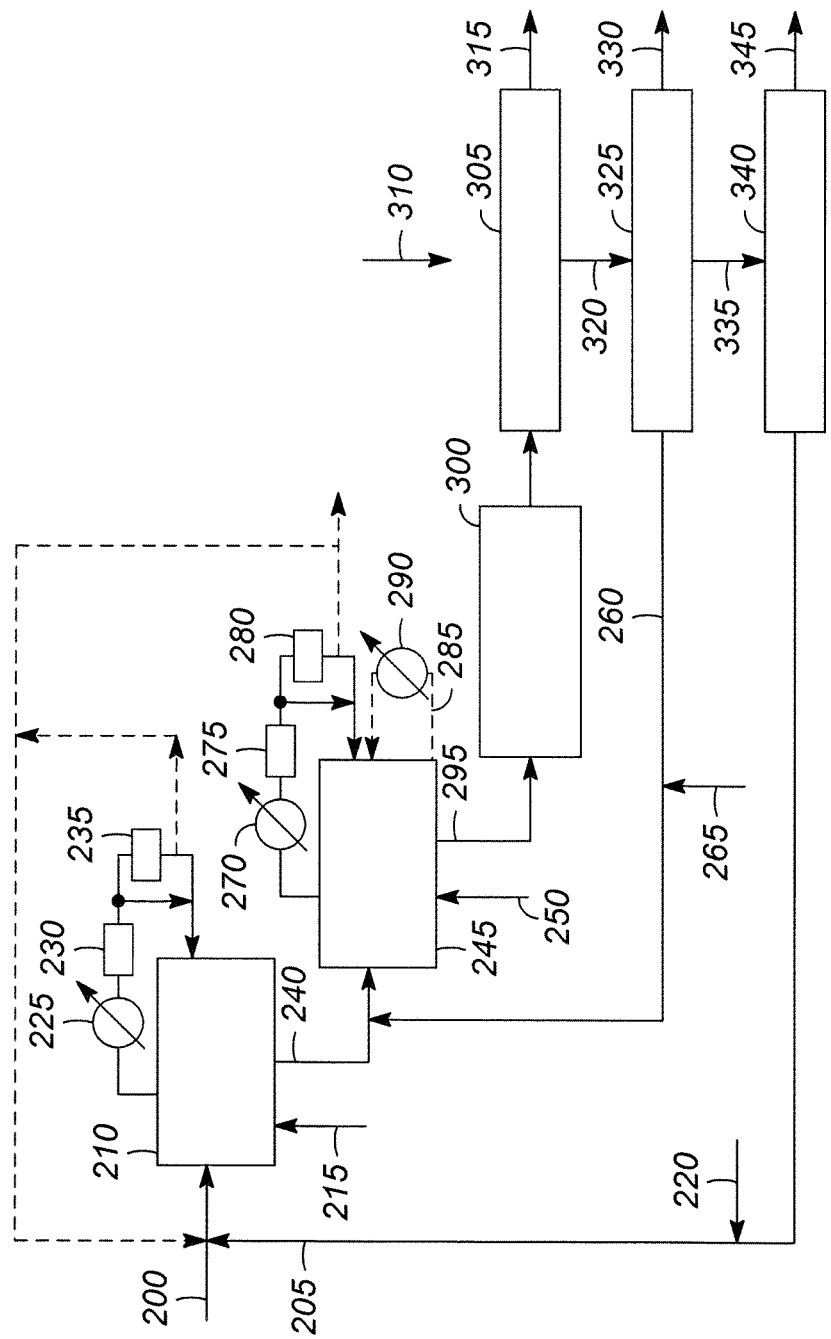
FIG. 3 is a general process flow diagram for another embodiment of a process for producing purified oxidized alkyl aromatic compounds.

FIG. 3 is a general process flow diagram for an embodiment having two reaction zones.

In some embodiments, any type of process can be used in the first reaction zone. For example, any of the commercially available processes discussed in the patents cited above or elsewhere can be used, if desired.

In other embodiments, an oxidation process as described is used.

Feed 200, including p-xylene, a carboxylic acid solvent, a catalyst, a bromine source, and an oxidizing agent 215 if present, enters the first reaction zone 210. The overhead condenser 225 removes heat from the reflux stream to control reaction zone temperature, and an absorption zone 230 and dehydration zone 235 remove offgas and water from the reaction zone.

The product from the first reaction zone, which is a p-xylene stream enriched with p-toluic acid, is used as the feed 240 for the second oxidation reaction zone 245. The feed can include a carboxylic acid solvent, an ionic liquid solvent, a catalyst, and a bromine source. The feed to the second oxidation reaction zone 245 also includes an oxidizing agent 250, and recycled ionic liquid stream 260. The ionic liquid solvent stream 260 can include make-up ionic liquid 265 as well as recovered ionic liquid.

The solvent in the second oxidation reaction zone 245 can include carboxylic acid solvent and ionic liquid. Compared to conventional processes, the amount of the carboxylic acid solvent is decreased when ionic liquids are used to avoid excessive solvent volumes.

The overhead condenser 270 removes heat from the reflux stream of the second oxidation reaction zone 245 to control the reactor temperature, and an absorption zone 275 and dehydration zone 280 remove offgas and water from the reaction zone.

The second oxidation reaction zone 245 can include a stream 285 to a heat exchanger 290 which is then returned to the second oxidation reaction zone 245. Depending on the reaction zone design, the cooler recycle stream can return to the vapor space, an upper stage of the reaction zone, or an appropriate location in a plug-flow reaction zone.

Effluent mixture 295 from the second oxidation reaction zone 245 is sent to a crystallization zone 300 to complete the crystallization process. The crystallization zone 300 can include one or more post reaction zones and/or one or more crystallizers. If a post reaction zone is needed to increase conversion further, additional oxidizing agent will be required. The post reaction zone can operate at lower pressure and lower temperature to help with crystallization. One or more crystallizers are used to complete the crystallization of the terephthalic acid at lower temperatures.

The crystallized product is separated from the solvent in a separator zone 305. The separator zone 305 can include one or more of filters, centrifuges, and dryers, as is known in the art.

Solvent 310 is used to wash the product crystals in the separator zone 305. The purified product 315 is dried and stored in the product silo. An additional separation device may be needed to ensure that the product meets the product specification before storage.

The washed mother liquor 320 is sent to solvent separator zone 325. The ionic liquid 260 is recycled back to the second oxidation reaction zone 245, and optionally the first oxidation reaction zone depending on the process being used in the first reactor. Make-up ionic liquid 265 can be added as needed.

The catalyst 330 is sent for catalyst recovery.

The carboxylic acid solvent 335 is dehydrated in a dehydration zone 340. The carboxylic acid solvent 205 can be recycled back to the first oxidation reaction zone 210. Make-up carboxylic acid solvent 220 can be added if needed. The waste water 345 is removed.

The first and second reaction zones can be in different reactors, if desired. However, the addition of a second titanium reactor significantly increases the cost of the process. In addition, it may not be easily possible to add a second reactor in an existing plant.

Figure 4:
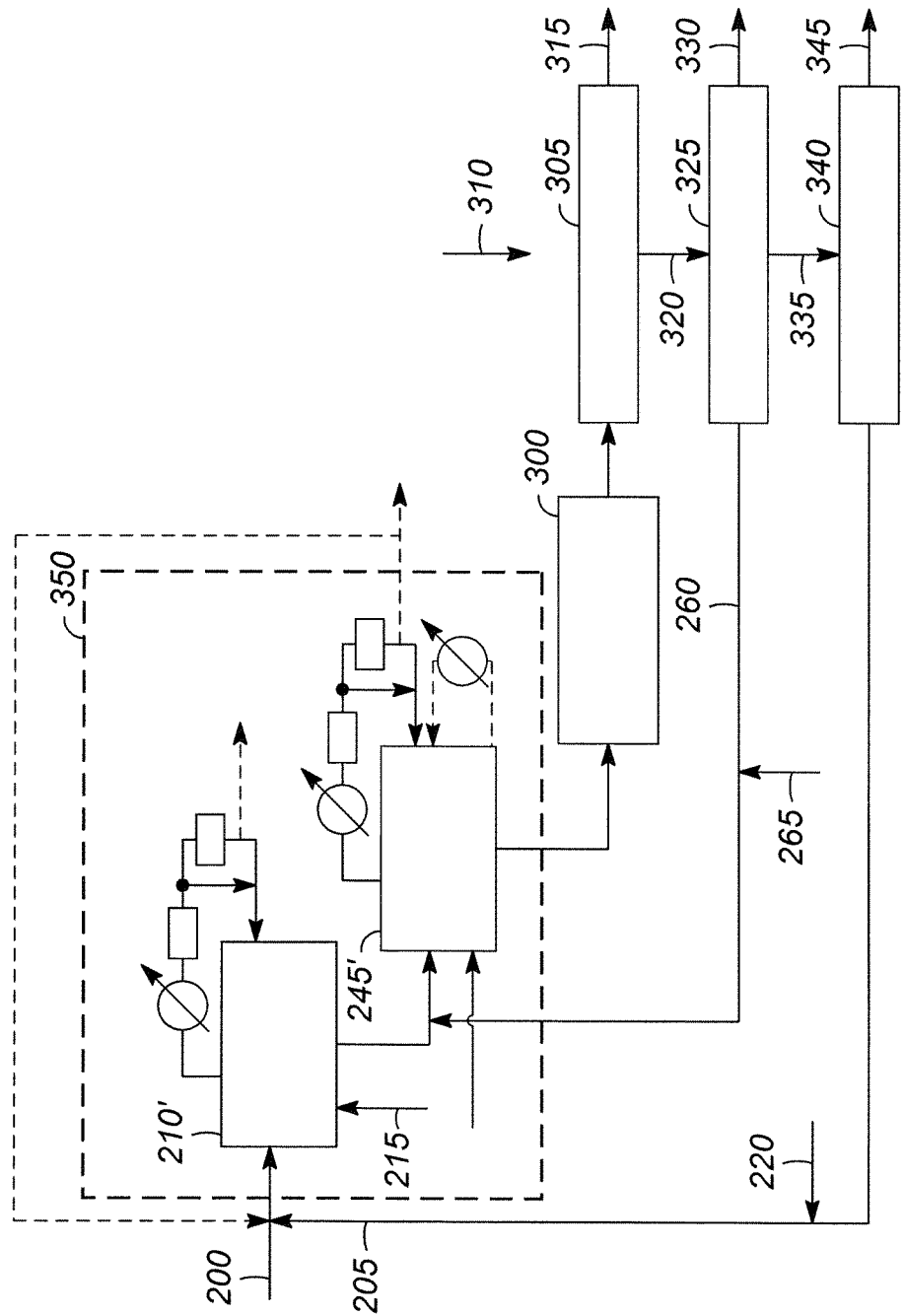
FIG. 4 is a process flow diagram for an embodiment having a single reactor.

Therefore, the first and second reaction zones can be in a single reactor, if desired. As illustrated in FIG. 4, the two reaction zones 210' and 245' are two zones in a single reactor 350. By properly designing the two zones, the same result can be obtained.

Figure 5:
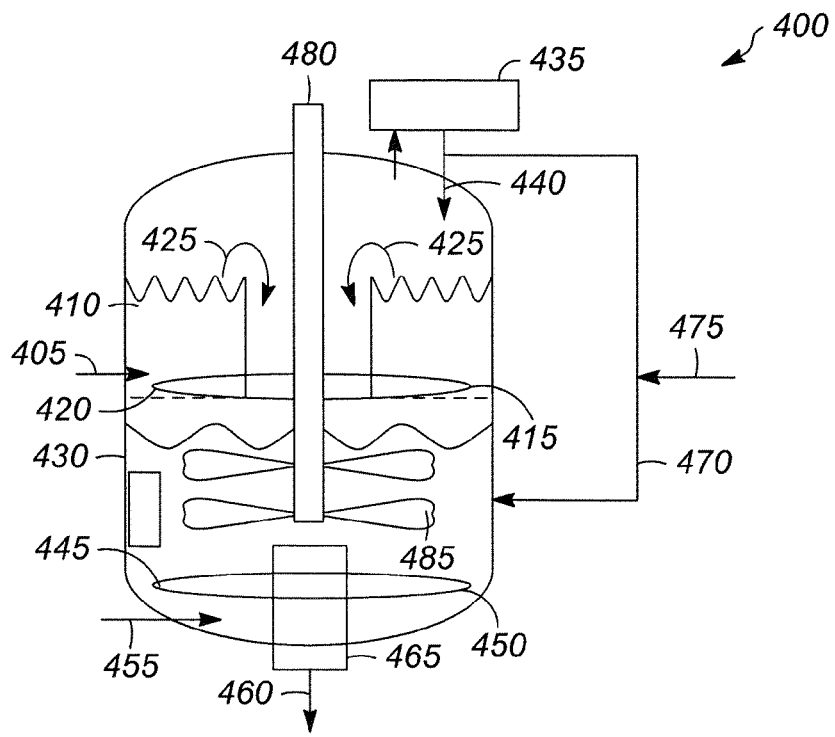
FIG. 5 is an illustration of one embodiment of a two zone continuous stirred tank reactor.

FIG. 5 illustrates an embodiment of a continuous stirred tank reactor (CSTR) 400 with a two zone design. The feed 405 enters the first reaction zone 410, such as an annulus. The feed 405 includes the alkyl aromatic compound with catalyst and carboxylic acid as solvent. An oxidizing agent 415 enters the first reaction zone 410 through a gas distributor ring 420, if needed. After a short residence time, for example, less than about 10 to about 40 min., the reactants and product 425 from the first reaction zone 410 overflow and enter the second reaction zone 430. If p-xylene is used as the starting material, the main product from the first reaction zone 410 should be p-toluic acid, which will react further in the second reaction zone 430 to generate terephthalic acid. Overhead carboxylic acid and water will be condensed in the condenser 435 and returned 440 to the first reaction zone 410. The condenser 435 is located at the top of the reactor 400 to minimize solid carryover. The reaction time in the second reaction zone is typically longer than that in the first reaction zone, for example, more than about 10 min. The reaction conditions in the first and second reaction zones are similar to those discussed below.

The second reaction zone 430 is on level control. There is a second distribution ring 445 to introduce the oxidizing agent 450 into the second reaction zone 430. Vapor from the second reaction zone 430 bubbles up through the first reaction zone 410 to provide proper mixing for the first reaction zone 410. Mother liquor and ionic liquid solvent 455 enter near the bottom of the second reaction zone 430 and mix with the feed 425 coming from the first reaction zone 410. The product 460 of the second reaction zone 430 goes out through an internal or external deaerator 465. In order to control the ionic liquid to carboxylic acid ratio, a certain amount of carboxylic acid from the condenser 420 can return 470 to the second reaction zone 430, with make-up carboxylic acid 475, if needed.

The CSTR reactor includes an impeller 480 with baffles 485 to mix the contents of the second reaction zone 430.

Figure 6:
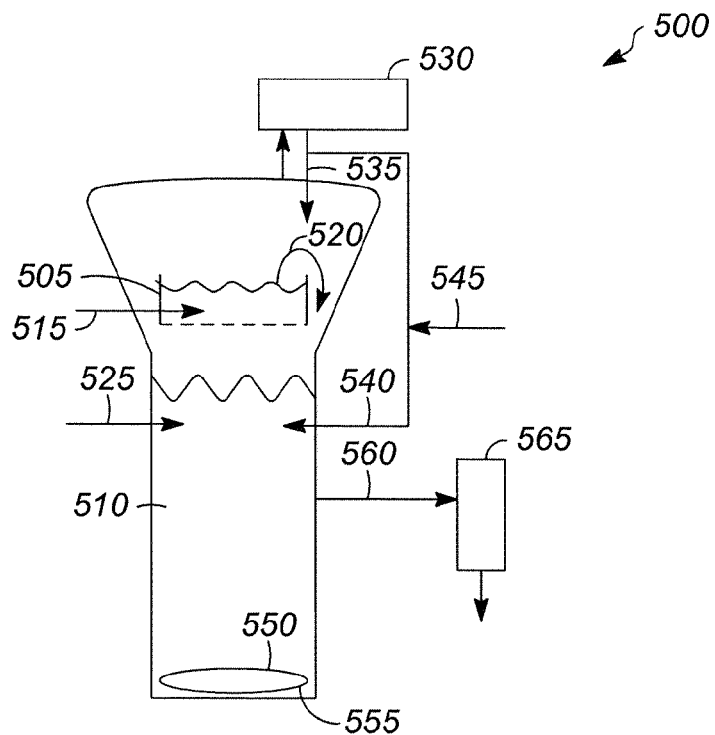
FIG. 6 is an illustration of one embodiment of a two zone plug flow bubbling reactor.

FIG. 6 shows a two zone plug flow bubbling reactor 500 which include a first reaction zone 505 and a second reaction zone 510. The feed 515, including the alkyl aromatic compound, carboxylic acid solvent, and catalyst, enters the first reaction zone 505. AN oxidizing agent is added to the first reaction zone 505. The first reaction zone 505 is positioned above the second reaction zone 510. The reactants and product 520 flow over the top of the first reaction zone 505 and into the second reaction zone 510. The feed 525 for the second reaction zone 510, which includes ionic liquid solvent and mother liquor, is introduced near the top of the second reaction zone 510. Overhead acetic acid and water are condensed in the condenser 530 and returned 535 to the first reaction zone 505.

There is a distribution ring 550 to introduce an oxidizing agent 555 into the second reaction zone 510. Vapor from the second reaction zone 510 bubbles up through the first reaction zone 505 to provide proper mixing for the first reaction zone 505. The product 560 of the second reaction zone 510 goes out through an internal or external deaerator 565 at about the middle of the second reactor zone 510. In order to control the ionic liquid to carboxylic acid ratio, carboxylic acid 540 from the condenser 530 can return to the second reaction zone 510, with make-up carboxylic acid 545, if needed.

The product recovery process and equipment would be similar to that described above for the two reactor system.

The solvent comprises at least one ionic liquid. Two or more ionic liquids can be used, if desired.

Generally, ionic liquids are non-aqueous, organic salts composed of ions where the positive ion is charge balanced with a negative ion. These materials have low melting points, often below 100° C., undetectable vapor pressure, and good chemical and thermal stability. The cationic charge of the salt is localized over hetero atoms, and the anions may be any inorganic, organic, or organometallic species.

Most ionic liquids are formed from cations that do not contain acidic protons. The synthesis of ionic liquids can generally be split into two parts: formation of the desired cation, and anion exchange to form the desired product. Quaternization of an amine or phosphine, for example, is the initial step in the synthesis of the cation of an ionic liquid. If it is not possible to form the desired anion directly by the quaternization reaction, a further step is required.

There are estimated to be hundreds of thousands of simple ion combinations to make ionic liquids, and an almost endless ($10^{18}$) number of potential ionic liquid mixtures. This implies that it should be possible to design an ionic liquid with the desired properties to suit a particular application by selecting anions, cations, and mixture concentrations. Ionic liquids can be adjusted or tuned to provide a specific melting point, viscosity, density, hydrophobicity, miscibility, etc. for specific applications. The thermodynamics and reaction kinetics of processes carried out in ionic liquids are different from those in conventional media. This creates new opportunities for catalytic reactions, separations, combined reaction/separation processes, heat transfer agents, hydraulic fluids, paint additives, electrochemistry applications, as well as many others. Ionic liquids do not emit volatile organic compounds (VOCs), providing a basis for clean manufacturing, e.g., "green chemistry."

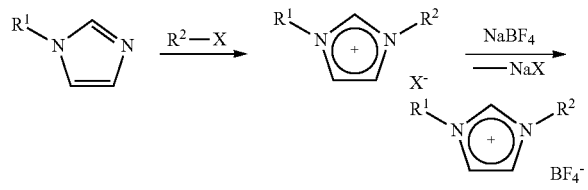

$R^1$ = methyl, vinyl, allyl $R^2$ = ethyl, propyl, butyl, isobutyl, propargyl, allyl, crotyl, methallyl X = Cl, Br The organic cation can comprise a linear, branched, or cyclic heteroalkyl unit, as described in U.S. Pat. No. 2010/0174111. The term "heteroalkyl" refers to a cation comprising one or more heteroatoms chosen from nitrogen, oxygen, sulfur, boron, arsenic, boron, antimony, aluminum, or phosphorous capable of forming a cation. The heteroatom can be a part of a ring formed with one or more other heteroatoms, for example, pyridinyl, imidazolinyl rings, that can have substituted or unsubstituted linear or branched alkyl units attached thereto. In addition, the cation can be a single heteroatom wherein a sufficient number of substituted or unsubstituted linear or branched alkyl units are attached to the heteroatom such that a cation is formed.

Non-limiting examples of heterocyclic and heteroaryl units that can be alkylated to form cationic units include imidazole, pyrazoles, thiazoles, isothiazoles, azathiozoles, oxothiazoles, oxazines, oxazolines, oxazaboroles, dithiozoles, triazoles, selenozoles, oxaphospholes, pyrroles, boroles, furans, thiphenes, phospholes, pentazoles, indoles, indolines, oxazoles, isothirazoles, tetrazoles, benzofuran, dibenzofurans, benzothiophenes, dibenzothoiphenes, thiadiazoles, pyrdines, pyrimidines, pyrazines, pyridazines, piperazines, piperidines, morpholines, pyrans, annolines, phthalazines, quinazolines, and quinoxalines.

The anionic portion of the ionic liquid can comprise an inorganic, organic, or organometallic moiety, as described in U.S. Pat. No. 2010/0174111. Non-limiting examples of anions include inorganic anions: halogens, (e.g., F, Cl, Br, and I); borides, $BX_4$, wherein X represents halogen, (e.g., $BF_4$, $BCl_4$), and the like; phosphates(V), $PX_6$; $PF_6$, and the like; arsenate(V), $AsX_6$; $AsF_6$, and the like; stibate(V) (antimony), $SbX_6$; $SbF_6$, and the like; $CO_3^{2-}$; $NO_2^{1-}$, $NO_3^{1-}$, $SO_4^{2-}$, $PO_4^{3-}$, $(CF_3)SO_3^{1-}$.

Other non-limiting examples of ionic liquid anions include substituted azolates, that is, five membered heterocyclic aromatic rings that have nitrogen atoms in either positions 1 and 3 (imidazolates); 1, 2, and 3 (1,2,3-triazolates); or 1, 2, 4 (1,2,4-triazolate). Substitutions to the ring occur at positions that are not located in nitrogen positions (these are carbon positions) and include CN (cyano-), $NO_2$ (nitro-), and $NH_2$ (amino) group appended to the heterocyclic azolate core.

Further non-limiting examples of anions include substituted or unsubstituted borides: $B(R)_4$; substituted or unsubstituted sulfates: $(RO)S(=O)_2O$; substituted or unsubstituted acyl units $RCO_2$, for example, acetate $CH_3CO_2$, proprionate, $CH_3CH_2CO_2$, butyrate $CH_3CH_2CH_2CO_2$, and benzylate, $C_6H_5CO_2$; substituted or unsubstituted phosphates: $(RO)_2P(=O)O$; substituted or unsubstituted carboxylates: $(RO)C(=O)O$; substituted or unsubstituted azolates wherein the azolate can be substituted on a carbon atom by a unit chosen from cyano, nitro, and amino. R can be an organic, inorganic, or organometallic group. Non-limiting examples of R include hydrogen; substituted or unsubstituted linear branched, and cyclic alkyl; substituted or unsubstituted linear, branched, and cyclic alkoxy; substituted or unsubstituted aryl; substituted or unsubstituted aryloxy; substituted or unsubstituted heterocyclic; substituted or unsubstituted heteroaryl; acyl; silyl; boryl; phosphino; amino; thio; and seleno.

In an embodiment, ionic liquids suitable for use include, but are not limited to, one or more of imidazolium ionic liquids, pyridinium ionic liquids, tetra alkyl ammonium ionic liquids, and phosphonium ionic liquids. More than one ionic liquid may be used. Imidazolium, pyridinium, and ammonium ionic liquids have a cation comprising at least one nitrogen atom. Phosphonium ionic liquids have a cation comprising at least one phosphorus atom. In an embodiment, the ionic liquid comprises a cation selected from alkyl imidazolium, di-alkyl imidazolium, and combinations thereof. In another embodiment, the ionic liquid comprises an anion selected from halides, acetate, carboxylates, and combinations thereof. The ionic liquid may comprise at least one of 1-butyl 3-methyl imidazolium acetate (BMImOAc), 1-butyl 3-methyl imidazolium bromide (BMImBr), 1-hexyl 3-methyl imidazolium acetate, and 1-hexyl 3-methyl imidazolium bromide.

The ionic liquid can be provided, or it can be generated in situ from appropriate precursors, or both. If it is generated in situ, the solvent comprises precursors of one or more ionic liquids. The ionic liquid precursors comprise a cation precursor, such as an alkyl imidazole, alkyl pyridine, alkyl amine, alkyl phosphine, and the like, and an anion precursor, such as alkyl or aryl halides or acetates. In an embodiment, the precursors are methyl imidazole and butyl bromide.

The mode of introducing the ionic liquid precursors may vary depending on the nature of the alkyl aromatics being oxidized and the nature and purity of the product desired. In one mode of addition, the cation precursors and the anion precursors (generally liquids at room temperature and pressure) are mixed with a carboxylic acid (for example, acetic acid) solvent and introduced into the oxidation reactor(s). In another mode of addition, the ionic liquid precursors may be mixed with the alkyl aromatic feed and introduced into the oxidation reactors. In another mode of addition, both cation and anion ionic liquid precursor components may be introduced into the bottom of the reactor without pre-mixing with any other oxidation reactor components such as the feed, carboxylic acid solvent, and catalyst package.

The solvent can also comprise a carboxylic acid. When carboxylic acids are used in the solvent, the amount of carboxylic acid is decreased compared with conventional processes in order to avoid excessive solvent volumes. The carboxylic acid desirably has from 1 to 7 carbon atoms. In an embodiment, the carboxylic acid comprises acetic acid. The solvent may contain more than one carboxylic acid. For example, the solvent may further comprise benzoic acid. In another embodiment, the carboxylic acid of the solvent is acetic acid.

In an embodiment, the solvent has a ratio of the carboxylic acid to the ionic liquid within a range of about 1:16 to 16:1 by weight, or about 1:9 to 9:1 by weight, or about 3:17 to 17:3 by weight, or about 1:4 to 4:1 by weight, or about 1:3 to 3:1 by weight, or about 3:7 to 7:3 by weight, or about 7:13 to 13:7 by weight, or about 2:3 to 3:2 by weight, or about 9:11 to 11:9 by weight, or about 1:1 by weight. In an embodiment, the solvent contains more than 5% by wt ionic liquid, or at least about 6% by weight ionic liquid, or at least about 10% by weight ionic liquid, or at least about 15% by weight ionic liquid, or at least about 20% by weight ionic liquid, or at least about 25% by weight ionic liquid, or at least about 30% by weight ionic liquid, or at least about 35% by weight ionic liquid, or at least about 40% by weight ionic liquid, or at least about 45% by weight ionic liquid. The amount of ionic liquid includes ionic liquid precursors, if present. The optional ionic solid or material capable of forming an ionic salt in solution discussed below, if present, is included in the amount of ionic liquid.

Optionally, an ionic solid, such as ammonium acetate ($NH_4OAc$) and/or ammonium bromide ($NH_4Br$), can be added to the mixture. Alternatively, a material which is capable of forming an ionic salt in solution can be added. The material can form the ionic salt in solution by combining with ions present in the solution. For example, in a solution containing bromide (for example in the form of HBr) or acetate ions (for example, in the form of acetic acid), ammonia could combine with the bromide or acetate ions forming ammonium bromide or ammonium acetate. The use of one or more ionic solids or materials capable of forming an ionic salt in solution provided an additional reduction in the level of impurities.

In an embodiment, the amount of ionic solid and material capable of forming an ionic salt in solution ranges from about 5 wt % to about 45 wt %, relative to the weight of the solvent, or from about 10 wt % to about 45 wt %, relative to the weight of the solvent. The solvent includes the carboxylic acid, the ionic liquid and/or ionic liquid precursors, the optional ionic solid or material capable of forming an ionic salt in solution, and the optional water.

Optionally, the solvent may further comprise water. The water may be added to the mixture or generated in the mixture during the oxidation process. In an embodiment, the amount of water ranges from about 0.01 wt % to about 5 wt %, relative to the weight of the carboxylic acid. The amount of water may range from about 0.1 wt % to about 2 wt %, relative to the weight of the carboxylic acid.

In an embodiment, the ratio of solvent to p-xylene stream enriched with p-toluic acid in the mixture ranges from about 1:1 to about 10:1 by weight, or from about 1.5:1 to about 6:1 by weight, or from about 2:1 to about 4:1 by weight. The solvent includes the carboxylic acid, the ionic liquid and/or ionic liquid precursors, the optional ionic solid or material capable of forming an ionic salt in solution, and the optional water.

The catalyst comprises at least one of cobalt, manganese, titanium, chromium, copper, nickel, vanadium, iron, molybdenum, tin, cerium and zirconium. In an embodiment, the catalyst comprises cobalt and manganese. The metal may be in the form of an inorganic or organic salt. For example, the metal catalyst may be in the form of a carboxylic acid salt, such as, a metal acetate and hydrates thereof. Exemplary catalysts include cobalt (II) acetate tetrahydrate and manganese (II) acetate, individually or in combination. In an embodiment, the amount of manganese (II) acetate is less than the amount of cobalt (II) acetate tetrahydrate by weight.

The amount of catalyst used in the invention may vary widely. For example, the amount of cobalt may range from about 0.001 wt % to about 2 wt % relative to the weight of the solvent. In an embodiment, the amount of cobalt ranges from about 0.05 wt % to about 2 wt % relative to the weight of the solvent. The amount of manganese may range from about 0.001 wt % to about 2 wt % relative to the weight of the solvent. In an embodiment, the amount of manganese ranges from about 0.05 wt % to about 2 wt % relative to the weight of the solvent. In another embodiment, the ratio of cobalt to manganese ranges from about 3:1 to about 1:2 by weight on an elemental metal basis.

Bromine sources are generally recognized in the art as being catalyst promoters and include bromine, ionic bromine, e.g. HBr, NaBr, KBr, $NH_4Br$; and/or organic bromides which are known to provide bromide ions at the oxidation conditions, such as, benzylbromide, mono and di-bromoacetic acid, bromoacetyl bromide, tetrabromoethane, ethylene dibromide. In an embodiment, the bromine source comprises or consists essentially of or consists of hydrogen bromide. The amount of hydrogen bromide may range from about 0.01 wt % to about 5 wt %, relative to the weight of the solvent. In another embodiment, the amount of hydrogen bromide ranges from about 0.05 wt % to about 2 wt %, relative to the weight of the solvent. The solvent includes the carboxylic acid, the ionic liquid, the optional ionic solid or material capable of forming an ionic salt in solution, and the optional water.

Suitable oxidizing agents for the process provide a source of oxygen atoms to oxidize the p-xylene and/or p-toluic acid, and/or another intermediate oxidization product at the oxidation conditions employed. Examples of oxidizing agents include peroxides, superoxides, and nitrogen compounds containing oxygen such as nitric acids. In an embodiment, the oxidizing agent is a gas comprising oxygen, e.g. air, carbon dioxide, and molecular oxygen. The gas may be a mixture of gasses. The amount of oxygen used in the process is preferably in excess of the stoichiometric amount required for the desired oxidation process. In an embodiment, the amount of oxygen contacted with the mixture ranges from about 1.2 times the stoichiometric amount to about 100 times the stoichiometric amount. Optionally, the amount of oxygen contacted with the mixture may range from about 2 times the stoichiometric amount to about 30 times the stoichiometric amount.

At least a portion of the components provides a liquid phase, although dissolution of one or more of the mixture components may not be complete at any or some time during the process. The liquid phase may be formed by mixing the components at ambient conditions. In another embodiment, the liquid phase is formed as the temperature of the mixture increases to the oxidation temperature. A mixture of the components may be formed prior to the oxidation step, in the same or different vessel as that used in the oxidation step. In another embodiment, a mixture of the components is formed in an oxidation reactor, e.g. adding various streams of the components individually and/or in combination to a continuous or semi-continuous oxidation reactor. The combined components, and/or various streams of the components may be heated before they are mixed together.

Though many conventional alkyl aromatic oxidation processes are typically conducted in a mixed phase, and often include three phases (e.g. solid, gas, and liquid), they are frequently referred to in the art as "liquid phase" oxidation processes because the oxidation conditions are maintained to provide at least a portion of the mixture in the liquid phase. It is also known in the art that the number of phases present may vary over time during the process. Processes according to the instant invention may also be conducted in a liquid phase or mixed phase in a similar manner as known in the art.

Conventional, liquid phase oxidation reactors as known in the art may be used to practice the invention. Examples include vessels, which may have one or more mechanical agitators, and various bubble column reactors such as those described in U.S. Pat. No. 7,692,036. It is also known to design, operate, and control such reactors and the oxidation reaction for the oxidation conditions employed including, e.g., the temperature, pressure, liquid and gas volumes, and corrosive nature of the liquid and gas phases where applicable. See, e.g. U.S. Pat. No. 7,692,036 and U.S. Pat. No. 6,137,001.

The contacting step[s] can take place under oxidizing conditions, if desired. Suitable oxidizing conditions generally include a temperature ranging from about 125° C. to about 275° C. and a pressure ranging from about atmospheric, i.e. 0 MPa(g), to about 6 MPa(g) and a residence time ranging from about 5 seconds to about 2 weeks. That is, the mixture has a temperature and a pressure within these ranges and may be maintained within these ranges for a period of time within the residence time range. In another embodiment, the temperature ranges from about 175° C. to about 225° C.; and the temperature may range from about 190° C. to about 235° C. In an embodiment, the pressure ranges from about 1.2 MPa (g) to about 6.0 MPa (g); and the pressure may range from about 1.5 MPa (g) to about 6.0 MPa (g). In a further embodiment, the residence time ranges from about 10 minutes to about 12 hours. The oxidation temperature, pressure and residence time may vary based on a variety of factors including for example, the reactor configuration, size, and whether the process is, batch, continuous, or semi-continuous. An oxidation condition may also vary based on other oxidation conditions. For example, use of a particular temperature range may enable use of a different residence time range.

In an embodiment, the terephthalic acid produced by the instant invention may precipitate, crystallize, or solidify in a liquid phase mixture at the oxidation conditions and/or as the mixture cools. Thus, a mixture according to the invention may further comprise solid terephthalic acid. Other compounds, including color bodies, and other oxidation products may solidify with or be trapped in the solid oxidation product thus reducing the purity of the desired product. In an embodiment, the mixture comprises a liquid phase. The mixture may comprise a gas phase such as when the oxidizing agent is added as a gas. The mixture may comprise a solid phase e.g. a mixture component, an oxidation product, or a by-product fails to dissolve or solidifies in the mixture. In an embodiment, the mixture comprises a liquid phase, a solid phase and optionally a gas phase. In another embodiment, the mixture comprises a liquid phase and a gas phase.

As noted above and discussed below, it has been discovered that the invention may be used to produce an oxidation product having different amounts of contaminants relative to those observed in conventional processes. In addition, the invention provides new ways to control the level of various contaminants in the oxidation product. In an embodiment, a process according to the invention further comprises forming the oxidation product as a solid, optionally at the oxidizing conditions, to produce the solid oxidation product and a mother liquor. The solid oxidation product may be separated from the mother liquor, i.e. liquid phase, and the mother liquor of the process may be recycled and reused in the contacting step or other steps of the process described below.

Processes according to the invention, may comprise one or more additional oxidizing steps. In an embodiment, a second oxidation step includes a second oxidizing temperature that is lower than the temperature of the first oxidizing step. Processes according to the invention may include additional contacting steps of the invention as described herein, and/or the invention may be combined with other oxidizing steps such as conventional oxidizing steps known in the art. Multiple contacting and/or oxidation steps may be conducted in series and/or parallel and may be combined with other process steps such as purification steps described herein.

In another embodiment, the invention further comprises purifying the oxidation product. Purifying may comprise one or more additional steps to isolate and purify the oxidation product. Examples of purifying steps include: separating wherein the oxidation product is separated from the mother liquor or another liquid phase such as by filtration and/or centrifugation; washing wherein the oxidation product is washed, for example with water and/or another solvent component; drying the oxidation product; and hydrogenation processes. Although hydrogenation processes can be used for purification, they are less desirable than other purification methods due to the cost. Such additional processing steps have been described in the general literature and are well known to those of ordinary skill in the art to be used in various combinations to purify oxidation products of the invention. See for example, the references cited in this application and the art cited therein.

A purification step of the instant invention may further comprise one or more solvent contacting steps. A solvent contacting step comprises contacting an oxidation product, also including washed or dried solid oxidation products, with a third solvent comprising at least one of water, a carboxylic acid, an ionic liquid and/or ionic liquid precursor, and a mother liquor to produce a purified oxidation product. In an embodiment, the solvent of the solvent contacting step contains ionic liquid and carboxylic acid, and optionally mother liquor. The composition of the solvent for the solvent contacting step can be as described above for the contacting step.

Solvent contacting may leach impurities from the solid oxidation product, and/or the oxidation product may be partially or completely dissolved in the solvent. Solvent contacting conditions include a solvent contacting temperature. The solvent contacting temperature may be lower than the oxidation temperature. In an embodiment, the solvent contacting temperature is at least 20° C. lower than the oxidation temperature. Solvent contacting may be practiced for example in the one or more crystallizers that follow the oxidation reactor in some conventional processes. The oxidation product may solidify, precipitate, or crystallize in the solvent of the solvent contacting step.

The product made by the process, either initially or following one or more additional oxidizing and/or purification steps, can contain less than about 2500 ppm 4-CBA, or less than about 2000 ppm 4-CBA, or less than about 1500 ppm 4-CBA, or less than about 1000 ppm 4-CBA, or less than about 750 ppm 4-CBA, or less than about 500 ppm 4-CBA, or less than about 250 ppm 4-CBA, or less than about 100 ppm 4-CBA, or less than about 50 ppm 4-CBA, or less than about 25 ppm 4-CBA.

It should be noted that the terms "first", "second", and "third" etc. are being used to distinguish one component, or composition, or stage, or zone, or reactor etc. from another. It is not necessarily the case that a "second" stage or zone, for example, physically or temporally follows a "first" stage or zone. Depending on the context, it could be before or after, as would be understood by those of skill in the art.

EXAMPLES

The examples are presented to further illustrate some aspects and benefits of the invention and are not to be considered as limiting the scope of the invention.

Example 1

Experimental Procedure

In a fume hood, load a Parr reactor with the specified amounts of components for the given experiment seal the reactor. The Parr reactor includes a gas distributor to disperse the gas through a 1.6 mm opening into the liquid, a mechanical gas entrainment stirrer, and baffles to ensure thorough mixing. Install the Parr reactor in a heater assembly at room temperature and connect a gas supply line to the reactor and a condenser to the reactor outlet. During operation, gases exit the reactor through the condenser then a trap, then a back-pressure regulator. Connect a safety vent having a rupture disk, and thermocouples to the reactor. Connect a cooling water recirculator to the condenser and begin to recirculate cooling water. Pressure test the Parr reactor at room temperature and 1.4 MPa (g) (200 psig) using nitrogen until there is no decrease in pressure for 15 minutes. Set the back pressure regulator on the reactor outlet to the experimental pressure and pressure test the reactor under nitrogen.

Begin raising the reactor temperature to the experimental temperature under the nitrogen atmosphere. Always follow all instructions for the specific reactor including temperature and pressure limits. When the reactor reaches the desired temperature begin adding air at the experimental rate and monitor the reactor temperature and pressure for the duration of the test. During the test, the air flow into the reactor is maintained at 2500 standard $cm^3$ per minute, the pressure is maintained at 4.1 MPa (g), and the stirrer is maintained at 1600 rpm. At the end of the test shut off the heater, cut the air flow and allow the reactor to cool. When the reactor cools to less than about 35° C., open the back pressure valve, stop the cooling water, and remove and empty the reactor to obtain the solid oxidation product and mother liquor.

The mother liquor and products are filtered under vacuum to separate the solids and liquid. The solids are then mixed with approximately 100 cc deionized water at room temperature and decanted. The room temperature deionized water mixing and decanting is repeated two additional times. A fourth wash with deionized water is heated to approximately 95° C. for 30 minutes and then filtered. The solids are dried at 80° C. for 8-24 hours before analyzing.

Examples 2-3

Examples 2-3 were individual tests conducted using the equipment and procedure given in Example 1. The components of the mixture, given in grams, operating temperature, time, and air flow, and results are given in Table 1.

Example 2 p-Xylene used as the starting material under oxidizing conditions.

Example 3

Figure 7:
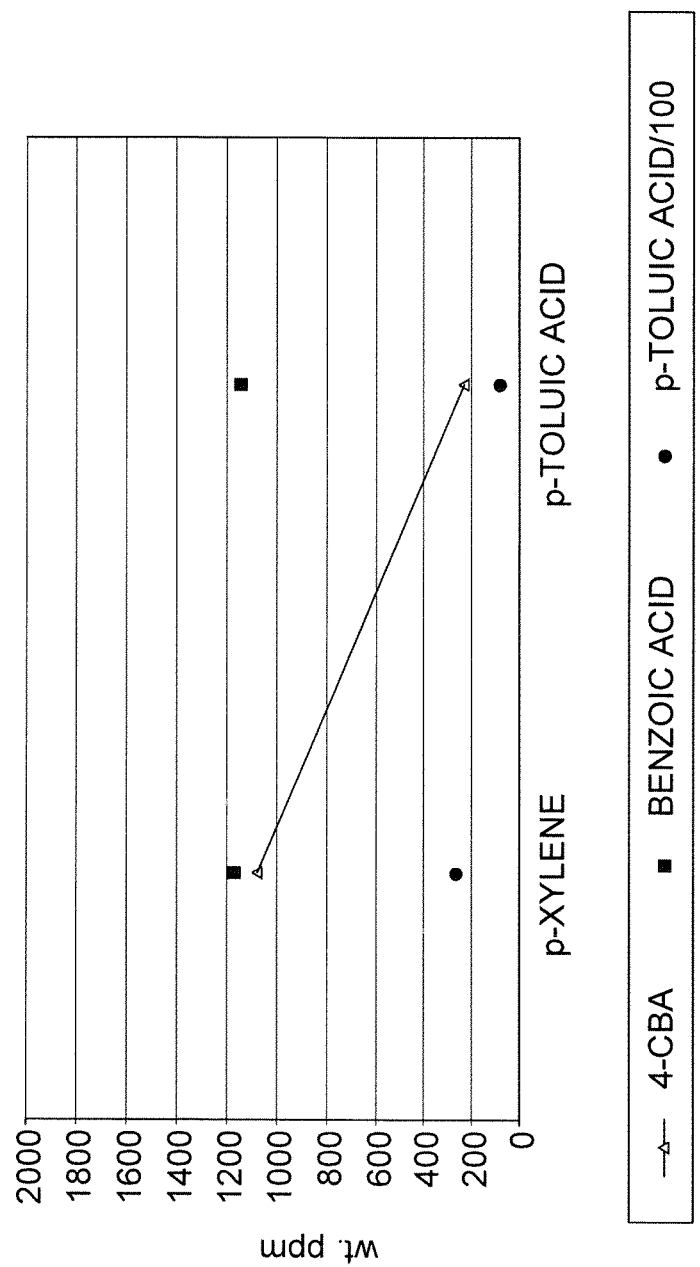
FIG. 7 is a graph showing the effect of starting material on levels of impurities.

Same oxidizing conditions as Example 2 except p-toluic acid was used as the starting material. The amount of 4-CBA, and p-toluic acid in the product dropped significantly, and the benzoic acid dropped slightly, as shown in FIG. 7. The recovery and the selectivity increased.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

TABLE 1

| | Example number | |
|---|---|---|
| | 2 | 3 |
| Oxidation Temperature, ° C. | 215 | 215 |
| Oxidation Time | 3 | 3 |
| Air Flow, sccm | 2500 | 2500 |
| Cooling | Fast | Fast |
| Components (g) | | |
| p-Xylene | 20 | |
| p-Toluic Acid | | 20 |
| Acetic Acid | 44 | 44 |
| BMImOAc | 20 | 20 |
| BMImBr | 16 | 16 |
| NH$_4$OAc | 12 | 12 |
| HBr | 0.4 | 0.4 |
| H$_2$O | 0.4 | 0.4 |
| Co(OAc)$_2$-4H$_2$O | 0.8 | 0.8 |
| Mn(OAc)$_2$ | 0.6 | 0.6 |
| Analysis of Product | | |
| Terephthalic acid (%) | 97.2 | 99.1 |
| 4-CBA (ppm) | 1081 | 230 |
| Benzoic acid (ppm) | 1163 | 1143 |
| p-Toluic acid (ppm) | 25,607 | 7183 |
| Visual Product Color | White | White |
| Recovery (%) | 85.2 | 91.0 |

What is claimed is:

1. A process for producing terephthalic acid comprising:
a first step of contacting p-xylene, a first solvent comprising a carboxylic acid, a first bromine source, a first catalyst, and a first oxidizing agent in a first reaction zone to produce a p-xylene stream enriched with p-toluic acid;
followed by a second step in which the p-xylene stream enriched with p-toluic acid is contacted with a second solvent comprising an ionic liquid, a second bromine source, a second catalyst, and a second oxidizing agent in a second reaction zone to produce a product comprising terephthalic acid, wherein the first reaction zone and the second reaction zone are in different reactors.

2. A process for producing terephthalic acid comprising:
contacting p-xylene, a first solvent comprising a carboxylic acid, a first bromine source, a first catalyst, and a first oxidizing agent in a first reaction zone to produce a p-xylene stream enriched with p-toluic acid;
contacting the p-xylene stream enriched with p-toluic acid, a second solvent comprising an ionic liquid, a second bromine source, a second catalyst, and a second oxidizing agent in a second reaction zone to produce a product comprising terephthalic acid wherein the ionic liquid is formed in situ from at least one ionic liquid precursor.

3. An apparatus for oxidizing alkyl-aromatic compounds consisting essentially of:
a first reaction zone having at least one inlet and at least one outlet;
a second reaction zone having at least one inlet and at least one outlet, at least one second reaction zone inlet in fluid communication with at least one first reaction zone outlet;
a purification zone having at least one inlet and at least one outlet, at least one purification zone inlet in fluid communication with at least one second reaction zone outlet, and at least one purification zone outlet in fluid communication with at least one first reaction zone inlet, or at least one second reaction zone inlet, or both.

4. The apparatus of claim 3 wherein the first reaction zone and the second reaction zone are in different reactors.

5. The apparatus of claim 3 wherein the first reaction zone and the second reaction zone are in a single reactor.

6. The apparatus of claim 5 wherein the reactor is a continuous stirred tank reactor, wherein the first reaction zone is an annulus reaction zone positioned above the second reaction zone, wherein vapor flow from the second reaction zone provides mixing in the first reaction zone, and wherein the second reaction zone has baffles for mixing.

7. The apparatus of claim 5 wherein the reactor is a plug flow reactor, wherein the first reaction zone is positioned above the second reaction zone, wherein vapor from the second reaction zone provides mixing in the first reaction zone.

8. The apparatus of claim 3 wherein the purification zone comprises at least one of a crystallization zone, a product separation zone, and a solvent separation zone.

9. The apparatus of claim 8 wherein the purification zone comprises:
a crystallization zone having at least one inlet and at least one outlet, at least one crystallization zone inlet in fluid communication with at least one second reaction zone outlet;
a product separation zone having at least one inlet and at least one outlet, the product separation zone comprising a filter, or a centrifuge, or both, at least one product separation zone inlet in fluid communication with at least one crystallization zone outlet;
a solvent separation zone having at least one inlet and at least one outlet, the solvent separation zone inlet in fluid communication with at least one product separation zone outlet and at least one outlet in fluid communication with at least one second reaction zone inlet.

10. An apparatus for oxidizing alkyl-aromatic compounds comprising:
a first reaction zone having at least one inlet and at least one outlet;
a second reaction zone having at least one inlet and at least one outlet, at least one second reaction zone inlet in fluid communication with at least one first reaction zone outlet;
a purification zone having at least one inlet and at least one outlet, at least one purification zone inlet in fluid communication with at least one second reaction zone outlet, and at least one purification zone outlet in fluid communication with at least one first reaction zone inlet, or at least one second reaction zone inlet, or both;
wherein the first and second reaction zones are in a single reactor;
and wherein:
the reactor is a continuous stirred tank reactor, wherein the first reaction zone is an annulus reaction zone positioned above the second reaction zone, wherein vapor from the second reaction zone provides mixing in the first reaction zone, and wherein the second reaction zone has baffles for mixing; or
the reactor is a plug flow reactor, wherein the first reaction zone is positioned above the second reaction zone, wherein vapor from the second reaction zone provides mixing in the first reaction zone.

* * * * *